United States Patent [19]

Umber et al.

[11] Patent Number: 5,782,836
[45] Date of Patent: Jul. 21, 1998

[54] RESECTING TOOL FOR MAGNETIC FIELD ENVIRONMENT

[75] Inventors: Ray Umber, Arlington; Durrell G. Tidwell, Burleson; Larry Dale Estes, North Richland Hills; Townesend R. Scantlebury, Arlington, all of Tex.

[73] Assignee: Midas Rex Pneumatic Tools, Inc., Fort Worth, Tex.

[21] Appl. No.: 690,634

[22] Filed: Jul. 30, 1996

[51] Int. Cl.[6] .................................................. A61B 17/32
[52] U.S. Cl. .......................... 606/79; 606/180; 173/218; 415/904
[58] Field of Search .......................... 606/79, 80, 180; 415/200, 216.1, 904; 173/93.5, 104, 218, 221

[56] References Cited

U.S. PATENT DOCUMENTS 3,472,323  10/1969  Hall .................................... 173/221
3,752,241  8/1973   Bent ................................... 173/221
5,383,771  1/1995   Ghode et al. ....................... 418/15

*Primary Examiner*—Michael Buiz
*Assistant Examiner*—David O. Reip
*Attorney, Agent, or Firm*—James E. Bradley

[57] ABSTRACT

A pneumatic surgical tool for cutting bone during surgical procedures includes a pneumatic motor having a rotary shaft, a resecting tool having a cutting element rotated by the motor, a sleeve to surround and support the resecting tool, anti-friction bearings for further rotatably supporting the resecting tool, and a chuck for connecting the resecting tool to a spindle of the rotary shaft. The motor housing, rotor, spindle, and chuck are created from titanium. The bore of the housing and the cutting tip of the resecting tool have thin hard metal cases, such as titanium nitride, titanium aluminum nitride, or titanium carbon nitride.

12 Claims, 2 Drawing Sheets

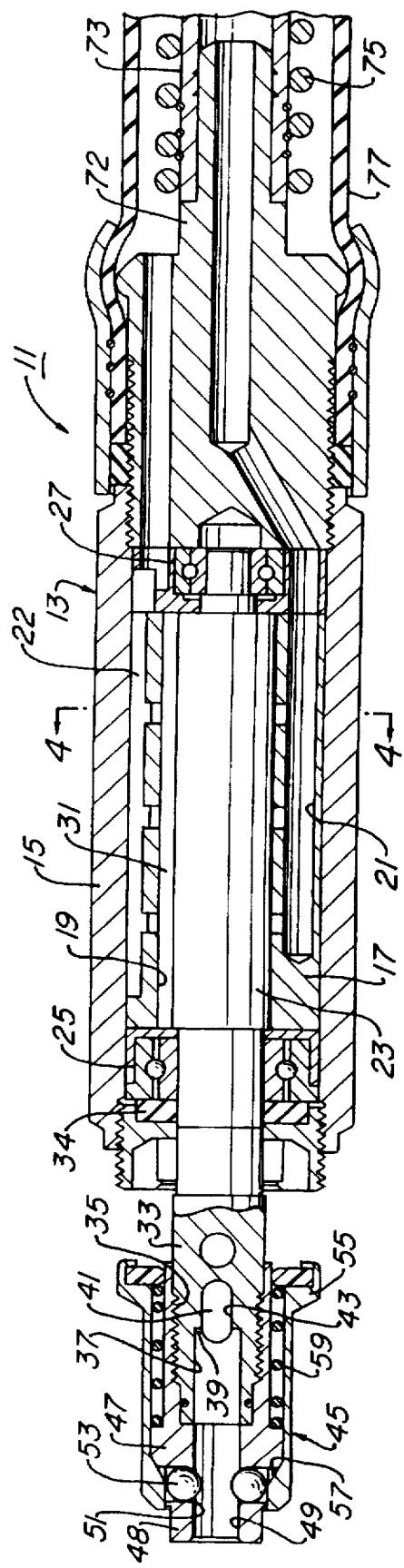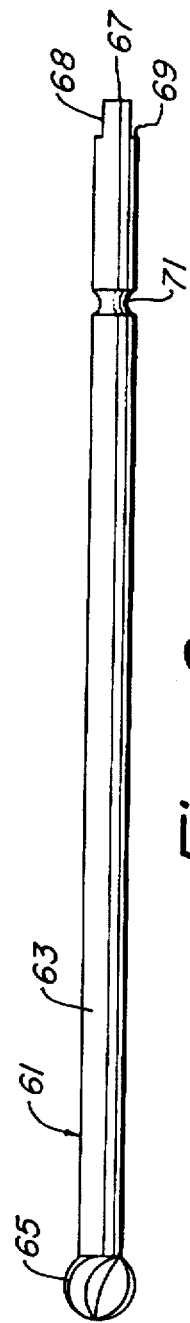

RESECTING TOOL FOR MAGNETIC FIELD ENVIRONMENT

TECHNICAL FIELD

The present invention relates in general to surgical instruments and, in particular, to a pneumatic resecting tool suitable for use in environments containing strong magnetic fields.

BACKGROUND ART

Surgical tools for use in the dissection of bone during surgical procedures are conventional in the art. Many such tools employ pneumatic motors to rotate the cutting element of a resecting tool. In their most basic form, such surgical instruments comprise a motor portion having a rotary shaft, a resecting tool having a cutting element, and means for connecting the resecting tool to a spindle or collet of the rotary shaft. These surgical instruments have been created from carbon steel because of the need for high material hardness and ability to withstand the wear of operating at high speeds. Also, thin hardened cases, such as titanium nitride and titanium aluminum nitride have been applied to the bore of the motor housing to reduce wear caused by the rotating vanes. In addition to steel, resecting tools in some instances have been formed of tungsten carbide.

A fairly recent diagnostic technique involves the use of magnetic resonance imaging (MRI) machines or other machines which create or utilize very high strength magnetic fields. These machines provide an image of internal organs of the human body. Surgeons may utilize the images from such machines to guide them in performing subsequent surgery. It would be advantageous to be able to simultaneously perform surgery using pneumatic resecting tools while the MRI is taking place. Also, the resident high magnetic field will attract magnetic objects potentially creating unguided missiles. However, because of the ferrous metal in the motors, these pneumatic resecting tools are not used.

For use during MRI operations, it would be very desirable to create surgical tools using nonferrous materials that would be unaffected by magnetic fields. Unfortunately, nonferrous metals are generally softer and wear more quickly. For this reason, nonferrous metals such as titanium have traditionally only been used in hand tools such as pliers and nippers, not in pneumatic resecting motors, which rotate at speeds.

DISCLOSURE OF INVENTION

A pneumatic surgical tool for the resection of bone during surgical procedures is driven by a pneumatic motor housing subjected to air pressure from an outside source which enters through air inlet passages and exits through air outlet passages in the housing. A rotary shaft or rotor is located within a bore in the motor housing and has an axis parallel to and offset from an axis of the bore. The rotary shaft has a spindle extending out of the motor housing and is rotatably supported by bearings. A resecting tool with a cutting element is connected to the spindle of the rotary shaft and rotated by the motor. A chuck connects to the spindle and secures the resecting tool.

The present invention improves the conventional surgical tool by creating substantially all of the components of the instrument from titanium. Preferably, the bore and the cutting tip of the resecting tool have thin hard metal cases to increase the hardness of the tool and its resistance to wear.

The thin coating is applied by known vapor deposition techniques and can be titanium nitride, titanium aluminum nitride, or titanium carbon nitride. The forward bearing is formed of beryllium copper and in one embodiment, the rearward bearing is formed of stainless steel.

BRIEF DESCRIPTION OF THE DRAWINGS

FIG. 1 is a partial cross-sectional side view of a pneumatic motor for a resecting tool constructed according to the present invention.

FIG. 2 is a side elevational view of a cutting tool constructed according to the present invention and for use with the motor of FIG. 1.

BEST MODE FOR CARRYING OUT THE INVENTION

Figure 3:
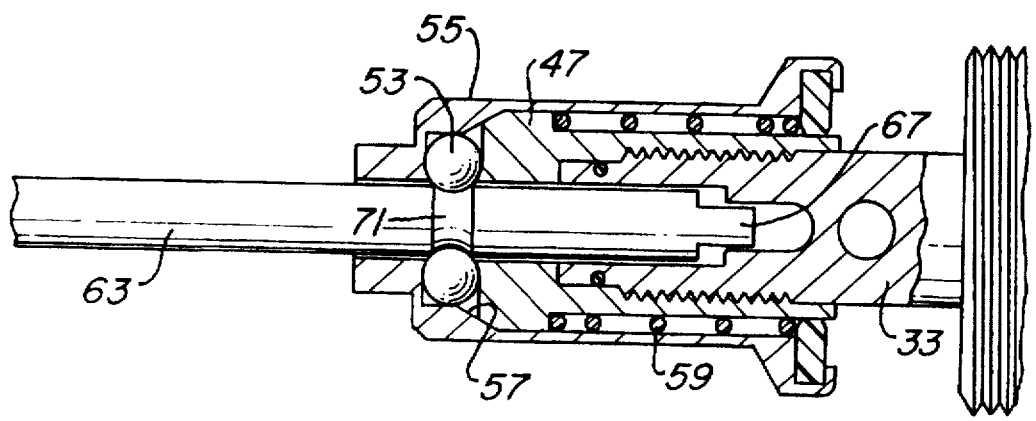
FIG. 3 is a partial cross-sectional side view of the chuck for the motor of FIG. 1, with the cutting tool of FIG. 2 secured therein.

Referring to FIG. 1, a surgical instrument 11 used for cutting bone in surgical procedures is shown. The surgical instrument 11 has a pneumatic driven motor 13 having a housing 17 surrounded by an outer sleeve 15, both formed of titanium. Motor housing 17 has a cylindrical bore 19. Pressurized air is supplied to bore 19 through a plurality of air inlet passages 21. Bore 19 also has a plurality of air outlet passages 22 opposite air inlet passages 21 for the discharge of pressurized air.

Figure 4:
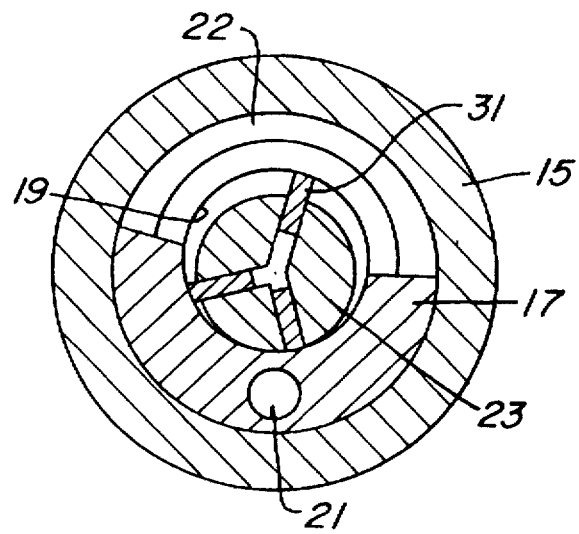
FIG. 4 is a cross-sectional view of the motor of the resecting tool of FIG. 1, taken along the line 4—4 of FIG. 1.

A rotor or rotary shaft 23 is located inside bore 19 and has an axis parallel to but offset from the axis of bore 19, as illustrated also in FIG. 4. The axis of rotor 23 is located closer to the side of bore 19 containing air inlet passages 21 and away from the side of bore 19 containing air outlet passages 22. Rotor 23 is also formed of titanium. Rotor 23 is rotatably supported in bore 19 by roller bearings 25, 27 which are axially spaced apart from each other. Roller bearing 25 is preferably of berrylium copper. In one embodiment, stainless steel was employed for the rearward bearing 27 without any significant detrimental effects on the magnetic field of the MRI machine.

As shown in FIG. 4, rotor 23 has three slots extending radially from the axis of rotor 23 and spaced 120 degrees apart from each other. A nonmetallic vane 31 is located inside each slot, and each vane 31 can slide radially inward or outward relative to the axis of rotor 23. As rotor 23 rotates inside bore 19, each vane 31 slides inward and outward such that it always remains in contact with the wall of bore 19. To avoid excessive wear, bore 19 has a hardened case of titanium nitride, titanium aluminum nitride, or titanium carbon nitride. The case is very thin, approximately 0.0001 inch. The case is formed by known vapor deposition techniques. The case has a hardness in the range from about 87 to 92 Rockwell "C".

A spindle 33 is connected to the end of rotor 23 extending out of bore 19. Spindle 33 protrudes from the forward end of motor 13 and is integrally formed with rotor 23. A permanent nonmetallic seal 34 is located in the forward end of outer sleeve 15 for sealing around rotor 23. A nonmetallic safety seal 34 is located outside outer sleeve 15, also for sealing against leakage of oil from the interior of housing 17. Safety seal 34 is removed after each use and replaced with a new seal.

Spindle 33 has a plurality of threads 35 on its exterior. A socket 37 extends into spindle 33. Socket 37 is cylindrical and has a shoulder or base 39 that is perpendicular to the axis of rotor 23. A slot 41 extends rearward from base 39. Slot 41 is generally rectangular, having two opposed flat faces 43 which serve as torque transmitting surfaces. Faces 43 are spaced equidistant from the axis of rotor 23.

A chuck 45 formed of titanium is secured to spindle 33. Chuck 45 has an inner sleeve 47 which has internal threads that mate with threads 35. Inner sleeve 47 has a protruding neck 48 which has a cylindrical axial passage 49. Passage 49 aligns with and is the same diameter as cylindrical socket 37. A plurality of apertures 51 are located in neck 48. Apertures 51 extend from passage 49 to the exterior and are spaced circumferentially apart.

A ball 53 is positioned within each aperture 51. Balls 53 are capable of moving inward, protruding into passage 49 as shown, and moving outward. In the outer, released position, balls 53 are radially outward of passage 49. An outer sleeve 55 is carried on inner sleeve 47. Outer sleeve 55 is capable of axial movement relative to inner sleeve 47 between a locked position shown in FIG. 1 and a released position, forward of the locked position. In the released position, a cam surface 57 on outer sleeve 55 moves forward of balls 53, allowing them to move to the released position. In the locked position shown, cam 57 retains balls 53 in the locked position. A spring 59 compressed between outer sleeve 55 and inner sleeve 47 urges outer sleeve 55 rearward to the locked position. Inner sleeve 47, outer sleeve 55, balls 53 and spring 59 are all formed with titanium.

Referring to FIG. 4, a resecting tool 61 is adapted to be coupled to spindle 33. Resecting tool 61 is formed of a nonferrous material, preferably titanium. Resecting tool 61 has a shaft 63 with a cutting tip 65 on its end. Preferably at least cutting tip 65 has a hardened case of titanium nitride, titanium aluminum nitride, or titanium carbon nitride. The case is very thin, approximately 0.0001 inch. The case is formed by known vapor deposition techniques in the same manner as the case on bore 19 of motor housing 17.

Resecting tool 61 also has a torque transmitting tang 67. Tang 67 is located on the axis of shaft 63, and has two flat sides 68 which face opposite each other. Tang 67 protrudes from a rearward facing shoulder 69. Tang 67 is adapted to be closely received within slot 41 (FIG. 3) with faces 68 in engagement with faces 43. A groove 71 extends circumferentially around shaft 63 for receiving balls 53.

Referring to FIG. 1, motor housing 17 has a rearward end that has a mandrel 72. An inner hose 73 of elastomeric material secures to mandrel 72. A stiffener spring 75 of nonferrous material encircles inner hose 73. An outer hose 77 is secured to housing 17, defining an annular passage surrounding inner hose 73.

In operation, air at about 100 psi is supplied through inner hose 73, with the air flowing through passages 21 to act against vanes 31. This causes rotor 23 to spin at a high speed. Air is exhausted through air outlet passages 22 and the annular space within outer hose 77. Rotor 23 rotates spindle 33, which in turn rotates resecting tool 61. The rotational force is transmitted by faces 43 against faces 68. Balls 53 and outer sleeve 55 retain shaft 63 against tension.

Surgical instrument 11 is capable of operating in a high strength field created by an MRI machine. Although the rearward set of bearings 25 may be of stainless steel, substantially all of the other components are of titanium, therefore are not influenced by the magnetic field.

The primary advantage of this invention is the nonmagnetic nature of titanium which allows use of these surgical instruments in the presence of magnetic fields without experiencing any external forces. Magnetic fields occur where magnetic resonance imaging (MRI) machines and other related devices are used. Another advantage is the lightweight nature of titanium relative to the typical ferrous materials used for surgical tools.

We claim:

1. A surgical instrument for resecting human bone within an environment containing a strong magnetic field, comprising:

a motor housing having a bore which has an axis;

a rotor rotatably mounted in the bore on spaced apart bearings, the rotor being located on an axis parallel to and offset from the axis of the bore, the rotor having at least one slot which extends radially from the rotor axis;

a spindle integrally formed with the rotor and extending from the motor housing;

at least one nonmetallic vane carried slidably in the slot of the rotor and having an edge which slidingly engages the bore;

an air inlet and an air outlet passage in the motor housing for delivering air pressure to and exhausting from the bore to cause the rotor to spin;

a chuck mounted to the spindle;

a resecting tool formed of a nonferrous material, having a shaft end that releasably couples to the chuck; and the motor housing, the rotor, the spindle and the chuck being formed of titanium so as to avoid being influenced by the magnetic field.

2. The surgical instrument according to claim 1, wherein the bore of the motor housing has a thin case of a material harder than titanium.

3. The surgical instrument according to claim 1, wherein a thin case of titanium nitride is located on the bore of the motor housing.

4. The surgical instrument according to claim 1, wherein a thin case of titanium aluminum nitride is located on the bore of the motor housing.

5. The surgical instrument according to claim 1, wherein the spindle is an integral portion of the rotor and comprises:

an axial cylindrical socket having a base perpendicular to the axis and a rectangular slot extending from the base and centered on the axis; and wherein the shaft of the resecting tool has a cylindrical portion which slides into the socket and a rectangular tang which extends from the cylindrical portion into the slot to transmit torque from the spindle to the resecting tool.

6. The surgical instrument according to claim 1, wherein the spindle is an integral portion of the rotor and comprises:

a set of external threads;

an axial cylindrical socket having a base perpendicular to the axis and a rectangular slot extending from the base and centered on the axis; and wherein the shaft of the resecting tool has a cylindrical portion which slides into the socket and a rectangular tang which extends from the cylindrical portion into the slot to transmit torque from the spindle to the resecting tool; and wherein the chuck comprises:

a sleeve having internal threads for engaging the external threads of the spindle; and means carried by the sleeve for engaging the shaft of the resecting tool to withstand tension applied to the shaft of the resecting tool.

7. The surgical instrument according to claim 1, wherein the spindle is an integral portion of the rotor and comprises:

a set of external threads;

an axial cylindrical socket having a base perpendicular to the axis and a rectangular slot extending from the base and centered on the axis; and wherein the shaft of the resecting tool has a cylindrical portion which slides into the socket, a rectangular tang which extends from the cylindrical portion into the slot to transmit torque from the spindle to the resecting tool, and a groove spaced axially from the tang; and wherein the chuck comprises:

an inner sleeve having internal threads for engaging the external threads of the spindle, the inner sleeve having a neck extending away from the spindle, the neck having a plurality of apertures spaced circumferentially around the neck;

a plurality of balls, each located in one of the apertures;

an external sleeve which is axially movable on the inner sleeve between an engaged position forcing the balls radially inward in the apertures into engagement with the groove on the shaft and a released position, allowing the balls to move radially outward in the apertures from the groove.

8. A surgical instrument for resecting human bone within an environment containing a strong magnetic field, comprising:

a motor housing having a bore which has an axis;

a rotor rotatably mounted in the bore on spaced apart bearings, the rotor being located on an axis parallel to and offset from the axis of the bore, the rotor having a plurality of slots which extend radially from the rotor axis;

a plurality of nonmetallic vanes carried slidably in the slots, each having an edge which slidingly engages the bore;

an air inlet and air outlet passage in the motor housing for delivering air pressure to the bore to cause the rotor to spin;

a spindle which is integrally formed with the rotor and extends from the motor housing, the spindle having a set of external threads, and a receptacle which has a cylindrical portion and at least one flat torque transmitting surface;

a chuck having internal threads which secure to the external threads on the spindle;

a resecting tool having a cutting tip and a shaft end which has a cylindrical portion that locates within the cylindrical portion of the receptacle and at least one flat surface parallel to the axis of the rotor which mates with said at least one torque transmitting surface in the spindle to transmit torque from the spindle to the resecting tool;

the chuck having tension means for engaging the shaft of the resecting tool to withstand tension applied to the shaft of the resecting tool;

the motor housing, the rotor, the spindle, the vanes, the chuck, and the resecting tool being formed of titanium so as to avoid being influenced by the magnetic field; wherein the bore of the motor housing has a thin case of a harder material than titanium to resist wear created by the sliding engagement of the vanes; and wherein the cutting tip of the resecting tool has a thin case of a harder material than titanium to resist wear.

9. The surgical instrument according to claim 8, wherein the shaft has a circumferential groove spaced axially from the flat surface on the end; and wherein the tension means comprises:

a plurality of balls carried within the chuck, movable between an engaged position with the groove on the shaft and a released position free of the groove; and a sleeve which holds the balls in the engaged position and which is axially movable relative to the spindle to allow the balls to move to the released position.

10. The surgical instrument according to claim 8, wherein the shaft has a circumferential groove spaced axially from the flat surface on the end; and wherein the tension means comprises:

an inner sleeve having a neck which protrudes from the spindle and which has a cylindrical passage for receiving the shaft and a plurality of circumferentially spaced apart apertures;

a plurality of balls carried within the apertures, movable radially between an engaged position with the groove on the shaft and a released position free of the groove; and an outer sleeve mounted to the inner sleeve which holds the balls in the engaged position and which is axially movable relative to the inner sleeve to allow the balls to move to the released position.

11. The surgical instrument according to claim 8, wherein:

said at least one flat torque transmitting surface comprises two radially spaced apart torque transmitting surfaces, each equidistant from the axis of the rotor; and said at least one flat surface on the shaft of the resecting tool comprises two flat surfaces, each for engaging one of the torque transmitting surfaces.

12. A method for resecting human bone within an environment containing a strong magnetic field, comprising:

providing a rotary surgical instrument having a motor housing made of titanium and having a bore which has an axis;

rotatably mounting a rotor made of titanium in the bore on spaced apart bearings on an axis parallel to and offset from the axis of the bore;

providing at least one nonmetallic sliding vane on the rotor;

forming a spindle integrally with the rotor, extending the spindle from the motor housing, and mounting a chuck made of titanium to the spindle;

inserting a resecting tool made of nonferrous metal into the chuck; and while the surgical instrument is located in the magnetic field, delivering air pressure to the bore of the motor housing to cause the rotor to spin, which rotates the chuck and the resecting tool, then engaging the resecting tool with the bone.

\* \* \* \* \*